United States Patent [19]

Kight

[11] Patent Number: 4,987,894
[45] Date of Patent: Jan. 29, 1991

[54] ANESTHETIC EVACUATION REGULATOR

[76] Inventor: John D. Kight, P.O. Box 941, Westwood, Calif. 96137

[21] Appl. No.: 333,918

[22] Filed: Apr. 6, 1989

[51] Int. Cl.[5] .................................................. A62B 9/02
[52] U.S. Cl. .............................. 128/205.24; 128/910; 52/198; 98/29; 98/37; 98/38.1; 98/42.06; 98/42.07
[58] Field of Search ....................... 128/203.12, 205.18, 128/205.19, 205.24, 910; 98/29, 37, 38.1, 42.06, 42.07, 42.1, 116; 52/198, 199, 302

[56] References Cited

U.S. PATENT DOCUMENTS

| | | | |
|---|---|---|---|
| 3,473,462 | 10/1969 | Imming | 98/42.06 |
| 3,785,377 | 1/1974 | Jorgensen | 128/910 |
| 3,800,793 | 4/1974 | Marrese et al. | 128/205.24 |
| 3,960,148 | 6/1976 | Dryden | 128/910 |
| 3,990,356 | 11/1976 | Keller | 98/42.1 |
| 4,109,651 | 8/1978 | Steigerwald . | |
| 4,151,843 | 5/1979 | Brekke et al. | 128/910 |
| 4,176,666 | 12/1979 | Hovey | 128/205.24 |
| 4,180,066 | 12/1979 | Milliken et al. . | |
| 4,219,020 | 8/1980 | Czajka . | |
| 4,446,861 | 5/1984 | Tada | 128/910 |
| 4,527,558 | 7/1985 | Hoenig . | |
| 4,538,605 | 9/1985 | Gedeon et al. | 128/910 |
| 4,593,688 | 6/1986 | Payton | 128/205.24 |
| 4,643,214 | 2/1987 | Blumenthal | 128/910 |

FOREIGN PATENT DOCUMENTS

| | | | |
|---|---|---|---|
| 2405441 | 5/1979 | France | 98/42.06 |
| 570170 | 12/1975 | Switzerland | 128/910 |
| 1552158 | 9/1979 | United Kingdom | 128/910 |
| 2178325 | 2/1987 | United Kingdom | 128/205.19 |
| 2208202 | 3/1989 | United Kingdom | 128/910 |

Primary Examiner—Eugene H. Eickholt

[57] ABSTRACT

The present invention is directed to an anesthetic evacuation device for use in situations where the anesthetic gasses are exhausted into the room air. More specifically, the invention discloses a device which can be attached to the popoff valve of many of the current anesthesia machines. The device contains and exhausts the excess anesthesia gases to the outside air, preventing any danger to medical personnel who may be in the same room. The system also allows for the rapid exhaust of any leftover gasses following the medical procedure.

10 Claims, 6 Drawing Sheets

ANESTHETIC EVACUATION REGULATOR

BACKGROUND OF THE INVENTION

1. Field of the Invention

The present invention relates to an anesthetic evacuation regulator, and more particularly pertains to the use of a device to control the exhaust of an anesthetic administering system into the air. In the field of anesthetic application, there is a hazard to the doctor due to the exhaust of anesthetic gases into the air. One such hazard exists in dentist offices where anesthetic is used to control pain during dental procedures. This is also a problem in veterinary offices where surgical cages are used to hold the animal during surgical procedures.

2. Description of the Prior Art

Various types of anesthetic evacuation regulators are known in the prior art. A typical example of such an anesthetic evacuation regulator is to be found in U.S. Pat. No. 4,180,066 which issued to Milliken et al. The Milliken patent discloses the use of a valve to control the exhausting of anesthesia gases. The device uses a spring loaded valve to control the flow of gases from the pop-off valve to the exhausting system. The device does not show the use of a simple anesthetic equalizer to control the exhaust flow. It also does not show the use of an easily adjustable valve which can be adjusted to help evacuate the waste gases following a procedure.

U.S. Pat. No. 4,219,020, which issued to Czajka, shows the use of another spring loaded circuit which exhausts anesthesia gases from a mask during the use of anesthesia. As with the Milliken device, it does not shown the novel features of applicant's invention.

U.S. Pat. No. 4,109,651, which issued to Steigerwald, shows the use of a waste gas evacuation system which is designed to attach itself to the ventilation bag of an anesthesia device. Owing to the nature of this device, it is neither as accurate or as convenient as the device of the applicant, which easily attaches to the waste gas (pop-off) valve currently in use on many anesthesia machines.

U.S. Pat. No. 4,527,558, which issued to Hoenig, shows the use of an exhaust device which attaches to the exhaust port of a normal anesthesia mask. The system uses a series of valves which control the exhausted gases of the patient. The important feature of this patent is the use of a surge reservoir which can contain a large volume of exhausted gases. The vacuum is then attached to this device to exhaust the gases. The use of the reservoir serves to avoid the need to adjust the vacuum level needed to exhaust the gasses without overcoming the spring loaded exhaust valves in the anesthesia system. The present invention utilizes an easily variable exhaust pressure which eliminates the need for this extra hardware since the vacuum can be adjusted to a low enough level to exhaust the air without opening the pop-off valve in the anesthesia system due to excess vacuum.

While the above mentioned devices are suited for their intended usage, none of these devices show the use of an easily adjustable anesthesia exhausting system. Furthermore none of the above system show the use of a system which is capable of driving multiple units at one time under different conditions. Additionally, none of the prior art devices disclose the use of an atmospheric equalizer valve which provides instant adjustment at the location of use of the amount of vacuum pressure being applied. Inasmuch as the art is relatively crowded with respect to these various types of anesthetic evacuation regulators, it can be appreciated that there is a continuing need for and interest in improvements to such anesthetic evacuation regulators, and in this respect, the present invention addresses this need and interest.

SUMMARY OF THE INVENTION

In view of the foregoing disadvantages inherent in the known types of anesthetic evacuation regulators now present in the prior art, the present invention provides an improved anesthetic evacuation regulator. As such, the general purpose of the present invention, which will be described subsequently in greater detail is to provide a new and improved anesthetic evacuation regulators which has all the advantages of the prior art anesthetic evacuation regulator and none of the disadvantages.

To attain this, representative embodiments of the concepts of the present invention are illustrated in the drawings and make use of an anesthetic evacuation device for use in situations where the anesthetic gasses are exhausted into the room air. More specifically, the invention deals with a device which can be attached to the pop off valve of many of the current anesthesia machines. This contains and exhausts the excess anesthesia gasses to the outside air, preventing any danger to medical personnel who must be in the same room. The system also allows for the rapid exhaust of any leftover gasses following the medical procedure.

The system consists of a small number of simple components. The first component is a base unit which may either be mobile or permanently mounted on an exterior wall of the building in which it is used. The second component is a vacuum producing motor which is contained in the base unit. A series of connecting pipes connect the vacuum producing motor to a remote location where the vacuum is needed. A vacuum control valve or atmospheric equalizer is connected between the exhaust system pipes and the pop-off valve of an anesthetic machine or animal operating cage.

The control valve or atmospheric equalizer determines how much vacuum is applied to the pop-off valve of a conventional anesthesia machine to assist in the exhausting of the anesthetic gases to the outside of the building. This allows the medical personnel to adjust the amount of vacuum in accordance with their needs.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved anesthetic evacuation regulator which has all the advantages of the prior art anesthetic evacuation regulators and none of the disadvantages.

It is another object of the present invention to provide a new and improved anesthetic evacuation regulator which may be easily and efficiently manufactured and marketed.

It is a further object of the present invention to provide a new and improved anesthetic evacuation regulator which is of a durable and reliable construction.

An even further object of the present invention is to provide a new and improved anesthetic evacuation regulator which is susceptible of a low cost of manufacture with regard to both materials and labor, and which accordingly is then susceptible of low prices of sale to the consuming public, thereby making such anesthetic evacuation regulators economically available to the buying public.

Still yet another object of the present invention is to provide a new and improved anesthetic evacuation regulator which provides in the apparatuses and methods of the prior art some of the advantages thereof, while simultaneously overcoming some of the disadvantages normally associated therewith.

Still another object of the present invention is to provide a new and improved anesthetic evacuation regulator which gives the user more complete control over the exhausting of the excess gases.

Yet another object of the present invention is to provide a new and improved anesthetic evacuation regulator which is easily adapted to serve multiple units simultaneously and provides each outlet with a different amount of vacuum according to the needs of the user.

Even still another object of the present invention is to provide a new and improved anesthetic evacuation regulator which can be used to help in the quick dissipation of anesthesia gases in situations where animals are sedated by use of an anesthesia cage.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
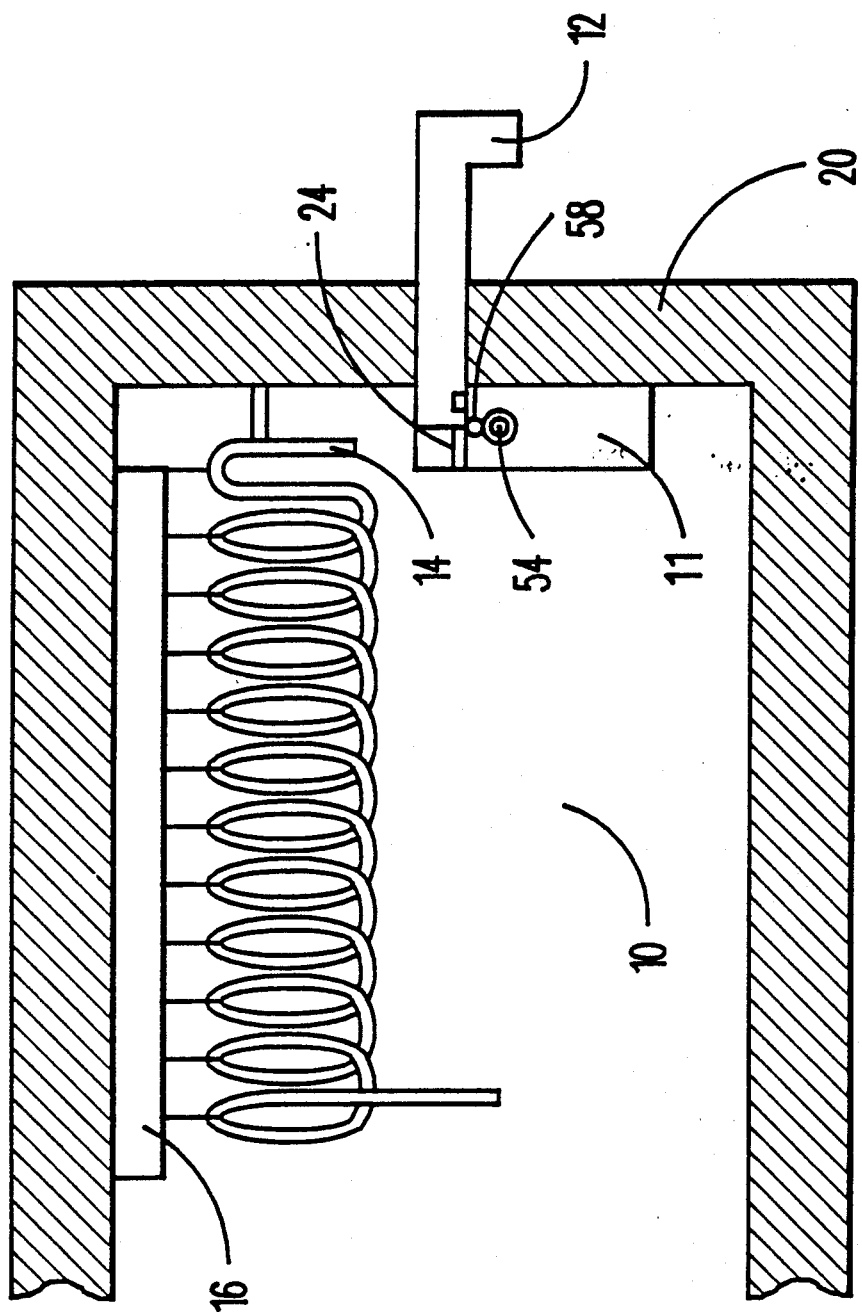
FIG. 1 illustrates the base vacuum source unit of the anesthetic exhaust system for use in hospitals or clinics.

With reference now to the drawings, and in particular to FIG. 1 thereof, a new and improved anesthetic evacuation regulator embodying the principles and concepts of the present invention and generally designated by the reference numeral 10 will be described.

More specifically, it will be noted that the first embodiment 10 of the invention includes a housing 11 which encloses a motor 32 (not shown) and an atmospheric equalizer to control the amount of vacuum present in the system. The motor drives a fan which produces an exhaust flow through the pipe outlet 24. Pipe outlet 24 is connected to outlet pipe 12 which extends through the exterior wall 20 of the building in which the device is installed. This allows the gasses which are collected to be vented through a hole in wall 20 to the outside of the building. The exhaust gases are collected through hose 14 which is connected during use to the vacuum port 54 located on the side of the housing 11. When the motor 32 is activated by use of switch 26 (FIG. 2) on the front of the housing, the fan driven by motor 32 produces an outlet flow through the exhaust pipe 12 and simultaneously produces a vacuum at the intake port 54. Hose 14 is attached to a hose handler 16 which allows the hose to be extended without dragging on the ground or interfering with the use of the device by medical personnel. During use, the distal end 18 of hose 14 is connected to the scavenger output of a "T" piece breathing, anesthetic dental mask or pop-off valve of an anesthetic machine. This allows the hose 14 to collect the exhaust gases which would normally be passed into the air within the building. This protects the medical personnel in the area from being exposed to the buildup of these gases during medical procedures.

Figure 2:
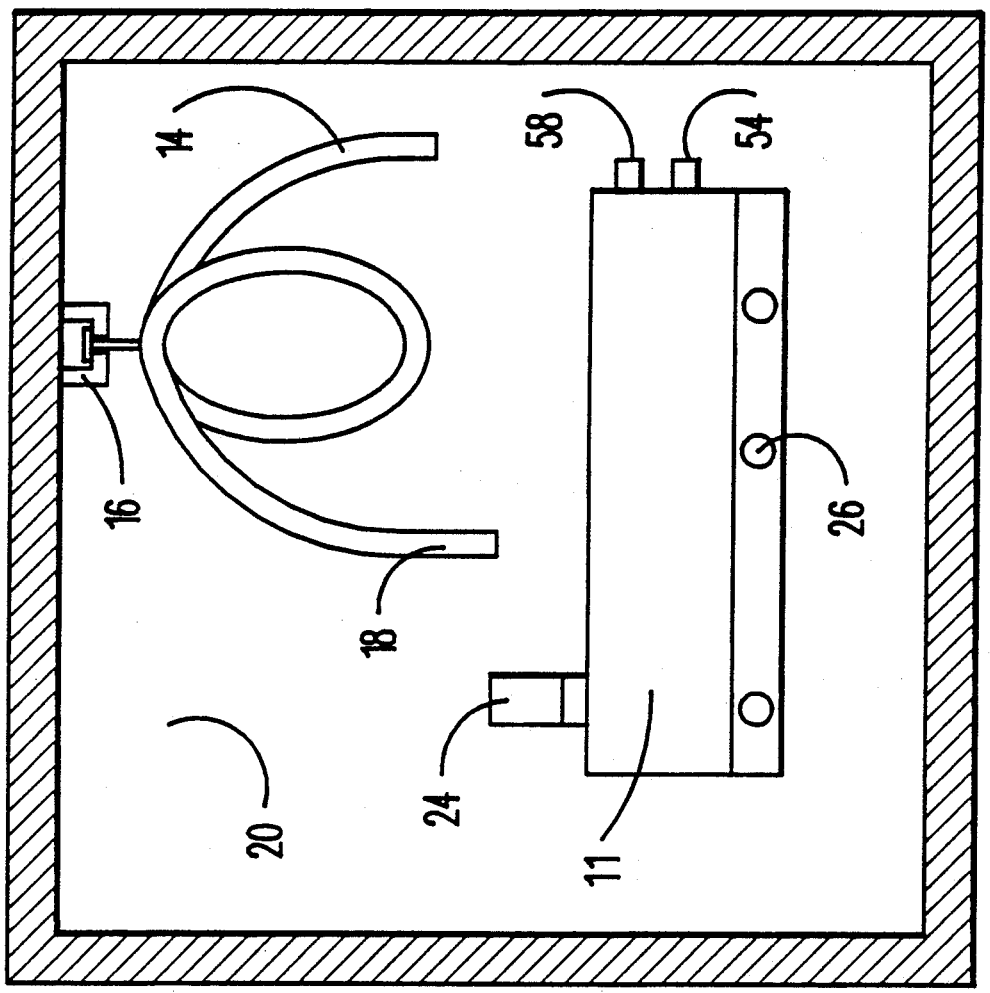
FIG. 2 is a side view of the device as shown in FIG. 1.

FIG. 2 illustrates a side view of the device shown in FIG. 1. During operation the hose 14 is connected at intake port 54 which is shown on the housing 11.

Figure 3:
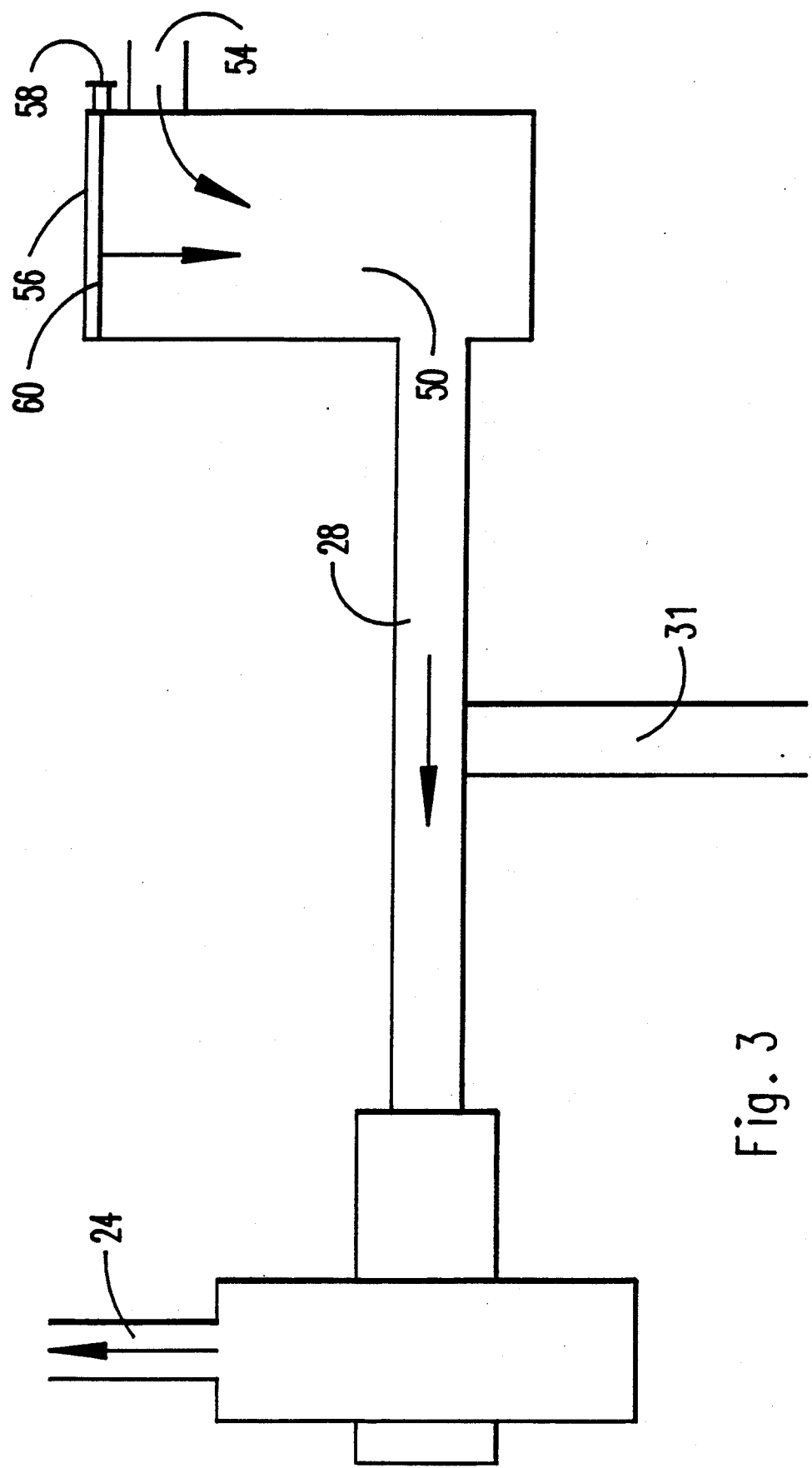
FIG. 3 is a diagram of the air flow through the vacuum source motor.

FIG. 3 is a flow diagram which illustrates the air flow into and out of the fan driven by the motor 32 to produce the vacuum. When the motor 32 is activated it produces a suction at intake 50 which is connected to the intake of the fan. The actual flow through the fan is controlled by the use of valve 60. This valve regulates, the flow of the air from the intake port 54 and also allows ambient air to be collected through ambient air intake 56 to keep the fan from overheating and preventing the collection of moisture in the plumbing. After the gases and cooling air pass through the fan housing, they are exhausted through the exhaust port 24 which is connected to the exterior vent pipe 12 (FIG. 1).

Figure 4:
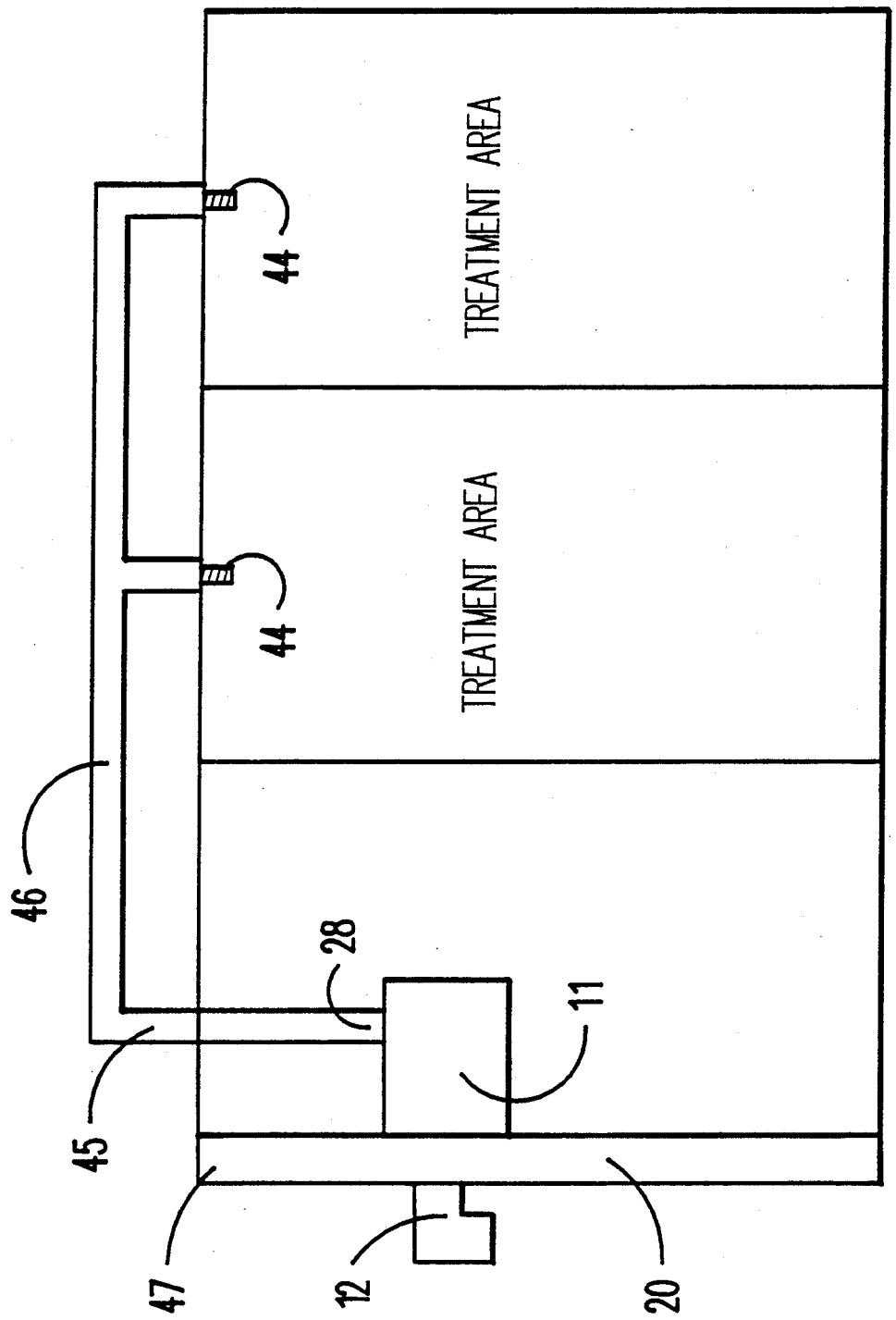
FIG. 4 is a view of an air control valve used to activate or deactivate an exhaust gas circuit.

FIG. 4 illustrates a second embodiment of the invention in which the device is arranged so that it may serve multiple users at one time. In this embodiment the housing 11 still contains a fan and motor which produce a vacuum at the intake port 28. In this case, however, the intake is connected to a manifold including a rigid pipe 45 which extends in the space above the ceiling 47 to adjoining treatment rooms in a typical medical environment. In the space above the ceiling, the pipe 45 connects to a set of distributions pipes 46 which terminate in each treatment room at a threaded connector 44. This allows the vacuum produced by the motor 32 to be readily accessible in each of the treatment rooms.

Figure 5:
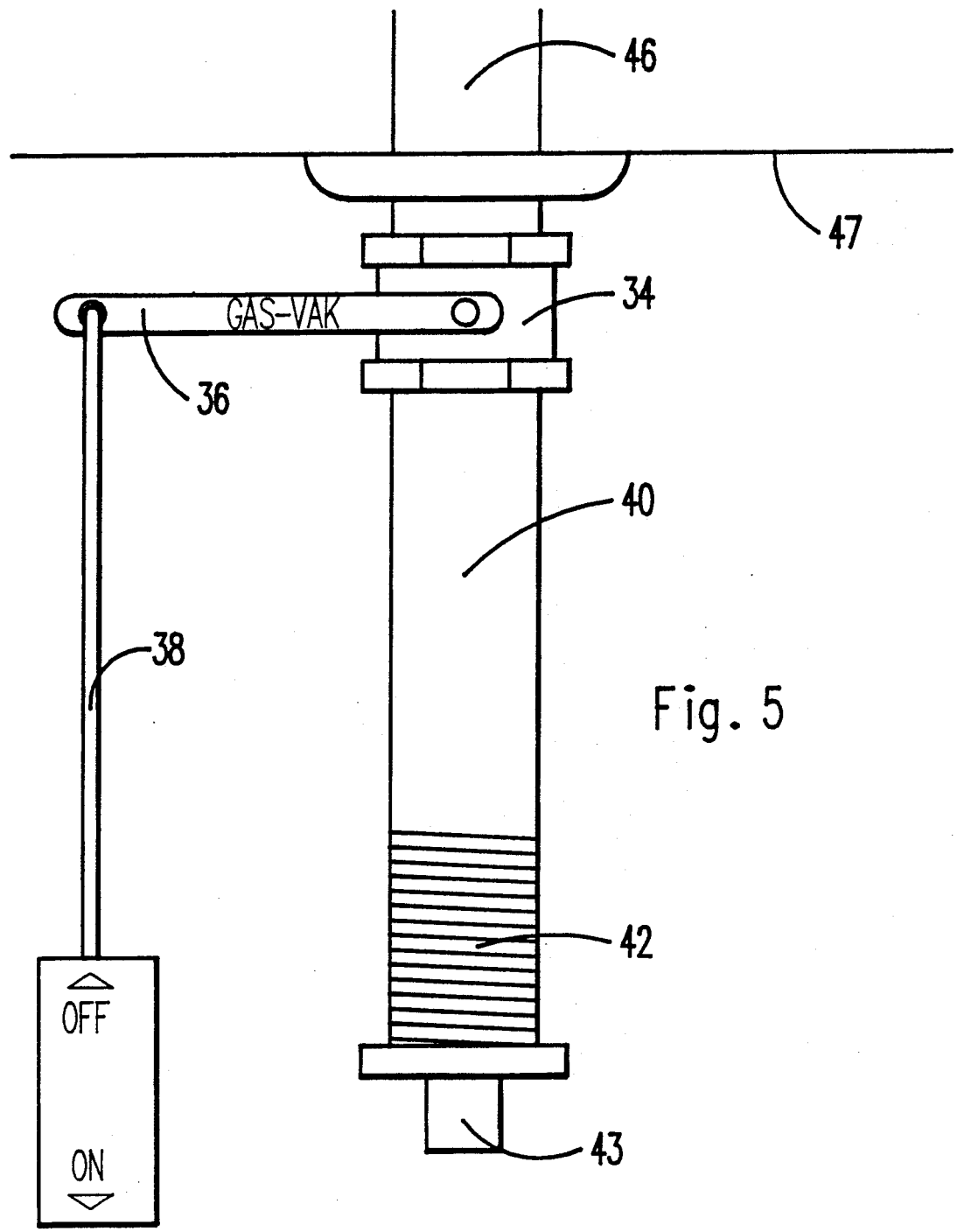
FIG. 5 is a view of an air handling system used in an alternative embodiment of the anesthetic evacuation device of the present invention.

To control the flow of air in each treatment room, a valve 40 (FIG. 5) is connected to the threaded connector 44. This valve has a butterfly type valve 34 which can open or close to connect the room with the vacuum source. This valve is operated by lever 36, which in turn is actuated by rod 38. Rod 38 is designed to be of sufficient length so that a normal sized person could reach up and pull it down to actuate the vacuum system. When the vacuum in no longer needed, the valve is closed by pushing up on rod 38 which in turn will close valve 34 to stop the exhaust flow. The flow, when actuated, is then passed through a flexible hose 42 which is connected to an atmospheric equalizer at its distal end 43.

Figure 6:
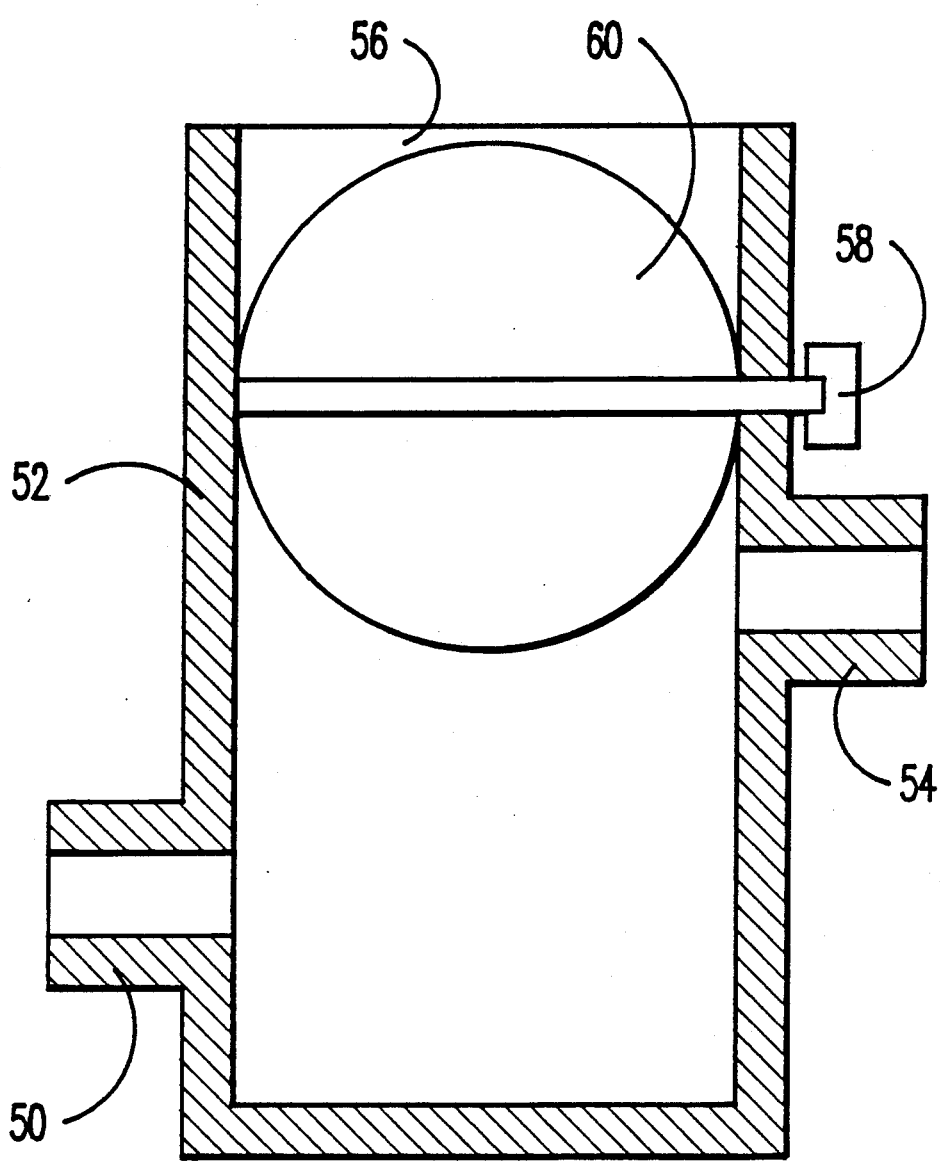
FIG. 6 illustrates an atmospheric equalizer used to control exhaust gas air flow.

FIG. 6 illustrates the atmospheric equalizer. The atmospheric equalizer is used to control the amount of vacuum which is applied to the waste gas input 54 and reduce high levels of vacuum to levels of less than 0.25" HG which is applied to the pop-off valve of the anesthetic machine, scavenger hose of a dental mask or "T" piece breathing circuit. The atmospheric equalizer is in the shape of a right circular cylinder with two pipe tees connected to it, one at each of two opposite sides. At the top end 56 there is an opening for ambient air to be drawn in. This allows the ambient air to be mixed with waste gases which are drawn in through waste input 54. The amount of air which is mixed with the waste gases is controlled by a knob 58 which controls a butterfly valve 60. If the valve 60 is fully open, the ambient air is almost 95% of the mixture which is passed through the exhaust port 50. If the valve is fully closed, the waste gasses account for fully 100% of the gases which are exhausted through port 50. This adjustable valve allows the user to control the amount of vacuum which is applied to the pop-off valve of the anesthetic machine. The adjustable nature of the device makes it very useful since it is more versatile. By setting the amount of vacuum low, the device may be used to exhaust the gases from a patient's mask without opening the spring loaded exhaust valve. If excess vacuum is produced, it will overcome the spring force of the anesthetic mask and exhaust gases before the patient can inhale them. This would interfere with the administration of the anesthetic. On the other hand, producing a large vacuum is useful too. In many veterinary offices, the animals are sedated by placing them in an anesthetic box which is then filled with anesthetic gases to produce unconsciousness in the animal patient. This box is usually just opened to the air to allow the gases to dissipate. By connecting the box to a vacuum port of the present invention and adjusting the equalizer 52 to produce a high suction, the gases could be quickly and safely exhausted without risk to the staff. During normal use, the atmospheric equalizer would be attached to a bracket on the anesthetic machine (not shown) to allow the flow to be quickly and easily adjusted according to the needs of the medical personnel involved. The equalizer 52 also allows ambient air to be mixed with the waste anesthetic gas, which, in an undiluted concentration, is corrosive to the plumbing of the exhaust gas system. For those hospitals which have in house suction, such as dental clinics and plastic surgery clinics, a vacuum flow meter (not shown) is inserted between the vacuum source and the exhaust port 50 of the atmospheric equalizer to control the amount of vacuum present in the system which is connected to the pop-off valve of the anesthetic machine or dental mask through intake port 54.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A new and improved anesthetic evacuation regulator adapted for connection with a pop-off valve of an anesthesia machine, said regulator comprising:
   a housing;
   a ducted motor driven fan in said housing for producing a vacuum;
   a vacuum port on said housing;
   a flexible hose connectable to said vacuum port for distributing the vacuum to a remote location;
   an atmospheric equalizer connected to said hose for controlling the amount of vacuum which is applied to the pop-off valve of an anesthetic machine; and
   said atmospheric equalizer including means for mixing the exhaust gas from the pop-off valve with ambient air.

2. A new and improved anesthetic evacuation regulator for use in controlling the exhaust of anesthetic gasses from anesthetic machines in a plurality of rooms in a treatment environment, said regulator comprising:
   a housing;
   means for producing a vacuum disposed in said housing;
   a series of pipes mounted in a ceiling of the treatment environment, said pipes connected to said vacuum source;
   said pipes including a vacuum port located in each of the treatment environment rooms;
   a butterfly valve connected to each of said vacuum ports;

a downwardly extending manually actuatable handle operably connected to each of said butterfly valves;

and an atmospheric equalizer including means for mixing the exhaust gas from a pop-off valve of an anesthetic machine with ambient air and for adjustably applying the vacuum to the pop-off valve.

3. The anesthetic evacuation regulator of claim 2, further comprising a flexible hose connected to the butterfly valve and to the atmospheric equalizer which controls the vacuum applied to the pop-off valve of the anesthetic machine.

4. The anesthetic evacuation regulator of claim 3, wherein the atmospheric equalizer comprises a right circular cylinder having:

one open end;

one closed end;

two cylindrical ports extending from the side of the cylinder;

each of the cylindrical ports being circumferentially spaced and disposed adjacent opposite ends of the cylinder;

the port near the open end being an intake port which is adapted for connection to a pop-off valve of an anesthetic machine;

the port near the closed end being a vacuum port which is connected to the vacuum source;

and a control means to control the mixing of ambient air with the waste gases collected from the pop-off valve of an anesthetic machine.

5. The anesthetic evacuation regulator of claim 4, wherein said control means comprises a butterfly valve disposed near the open end of said cylinder, above said intake port, which can be adjusted from a closed position in which no ambient air is allowed to enter from said open end, to a fully open position in which a large volume of ambient air is allowed to enter.

6. The anesthetic evacuation regulator of claim 5, wherein said control means is adapted for connection to an anesthetic cage to control the venting of gases therefrom.

7. An anesthetic evacuation regulator for regulating the exhaust of anesthetic gasses from a pop-off valve of an anesthesia machine, said regulator comprising;

a housing;

an intake port on said housing;

a ducted motor driven fan in said housing for producing a vacuum at said intake port;

distribution means for distributing the vacuum produced by the ducted fan, said distribution means comprising a flexible hose which is attached at one end to the intake port on the housing;

control means connected to the other end of said hose, said control means operative to adjust the amount of vacuum which is applied to a pop-off valve of an anesthetic machine;

and said control means including an atmospheric equalizer operative to adjustably mix ambient air with waste anesthesia gasses from the pop-off valve.

8. The anesthetic evacuation regulator of claim 7, wherein said atmospheric equalizer includes a valve operative to control the amount of ambient air which is mixed with the waste gas prior to being exhausted by the vacuum source.

9. The anesthetic evacuation regulator of claim 8, wherein said valve is a butterfly valve disposed upstream of the intake port.

10. The anesthetic evacuation regulator of claim 9, wherein the butterfly valve is adjustable between two extreme positions, one position which will result in the waste gases being all the exhausted gases and a second position in which the waste gases will be only a small percentage of the exhausted gases.

* * * * *